United States Patent
Ii et al.

(10) Patent No.: US 12,024,137 B2
(45) Date of Patent: Jul. 2, 2024

(54) VEHICLE, AND PASSENGER COMPARTMENT INTERIOR CLEANING DEVICE

(71) Applicant: TOYOTA JIDOSHA KABUSHIKI KAISHA, Aichi-ken (JP)

(72) Inventors: Yukinori Ii, Toyota (JP); Takeo Moriai, Nagakute (JP); Kazunori Mitomi, Toyota (JP); Yasuyuki Kamezaki, Toyota (JP); Kazuhide Tabata, Toyota (JP); Hiromi Nosaka, Okazaki (JP); Kenta Miyahara, Toyota (JP)

(73) Assignee: TOYOTA JIDOSHA KABUSHIKI KAISHA, Aichi-Ken (JP)

( * ) Notice: Subject to any disclaimer, the term of this patent is extended or adjusted under 35 U.S.C. 154(b) by 883 days.

(21) Appl. No.: 17/078,094

(22) Filed: Oct. 23, 2020

(65) Prior Publication Data

US 2021/0162959 A1    Jun. 3, 2021

(30) Foreign Application Priority Data

Dec. 3, 2019    (JP) ................. 2019-219072

(51) Int. Cl.
*B60S 1/64* (2006.01)
*A01M 1/20* (2006.01)
*A47L 7/00* (2006.01)
*A61L 2/10* (2006.01)
*A61L 2/26* (2006.01)

(52) U.S. Cl.
CPC ............... *B60S 1/64* (2013.01); *A01M 1/20* (2013.01); *A47L 7/0076* (2013.01); *A61L 2/10* (2013.01); *A61L 2/26* (2013.01); *A61L 2202/11* (2013.01); *A61L 2202/14* (2013.01); *A61L 2202/17* (2013.01); *A61L 2202/25* (2013.01)

(58) Field of Classification Search
CPC .... B60S 1/64; A01M 1/20; A61L 2/10; A61L 2/26; A61L 2202/11; A61L 2202/14; A61L 2202/17; A61L 2202/25; A61L 2/24; A61L 2/22; A61L 2/08; B60H 1/248; B60H 1/00742; B60H 3/0085; A47I 7/0076
See application file for complete search history.

(56) References Cited

U.S. PATENT DOCUMENTS

2012/0329381 A1    12/2012  Liao
2017/0210353 A1*  7/2017   Stauffer ................. B60N 2/58

FOREIGN PATENT DOCUMENTS

| CN | 201823091 U | 5/2011 |
| CN | 202016451 U | 10/2011 |
| CN | 203267730 U | 11/2013 |

(Continued)

*Primary Examiner* — David Redding
(74) *Attorney, Agent, or Firm* — HAUPTMAN HAM, LLP (57) ABSTRACT

A vehicle has: a communicating portion that communicates a passenger compartment interior with a passenger compartment exterior; a discharging device that, by operating, discharging at least one of dust or liquid which is within the passenger compartment through the communicating portion to the passenger compartment exterior; and a control section that, in a case of judging that there are no vehicle occupants within the passenger compartment, operates the discharging device, and causes dust within the passenger compartment to be discharged to the passenger compartment exterior.

7 Claims, 8 Drawing Sheets

(56) References Cited

FOREIGN PATENT DOCUMENTS

| | | | |
|---|---|---|---|
| CN | 107184147 | A | 9/2017 |
| JP | H516653 | A | 1/1993 |
| JP | 2002225540 | A | 8/2002 |
| JP | 200696067 | A | 4/2006 |
| JP | 2009166772 | A | 7/2009 |

* cited by examiner

VEHICLE, AND PASSENGER COMPARTMENT INTERIOR CLEANING DEVICE

CROSS-REFERENCE TO RELATED APPLICATION

This application claims priority under 35 USC 119 from Japanese Patent Application No. 2019-219072, filed on Dec. 3, 2019, the disclosure of which is incorporated by reference herein in its entirety.

BACKGROUND

Technical Field

The present disclosure relates to a vehicle and to a passenger compartment interior cleaning device.

Background Art

Japanese Patent Application Laid-Open (JP-A) No. 2002-225540 (Patent Document 1) discloses an air conditioner for a vehicle that has an inside air introducing mode and an outside air introducing mode. In this structure, when an abnormality signal of the air conditioner is received at the time of the cooling operation, the inside air introducing mode is interrupted, and the mode is switched to the outside air introducing mode.

SUMMARY

When air conditioning is carried out while introducing inside air as in aforementioned Patent Document 1, air within the passenger compartment is drawn-in by a blower being operated.

However, dust within the passenger compartment cannot be sufficiently eliminated by the output of the blower that is operated for inside air introduction. On the other hand, if the output of the blower is increased, there is the possibility of affecting the vehicle occupants who are within the passenger compartment.

In view of the above-described circumstances, an object of the present disclosure is to provide a vehicle and a passenger compartment interior cleaning device that, while removing dust that is within the passenger compartment, do not affect vehicle occupants.

A vehicle of a first aspect has: a communicating portion that communicates a passenger compartment interior with a passenger compartment exterior; a discharging device that, by operating, discharges at least one of dust or liquid which is within the passenger compartment through the communicating portion to the passenger compartment exterior; and a control section that, in a case of determining that there are no vehicle occupants within the passenger compartment, operates the discharging device, and causes dust within the passenger compartment to be discharged to the passenger compartment exterior.

In the vehicle of the first aspect, due to the discharging device operating, at least one of dust and liquid within the passenger compartment is discharged out to the passenger compartment exterior through the communicating portion that communicates the passenger compartment interior and the passenger compartment exterior. Due thereto, dust within the passenger compartment can be effectively removed merely by operating the discharging device.

Further, the discharging device is operated by the control section in a case in which it is determined that there are no vehicle occupants within the passenger compartment. Due thereto, even in a case in which, for example, the discharging device is operated and air within the passenger compartment is drawn-in with great force, cleaning can be carried out without causing the vehicle occupants discomfort. Note that what is called "communicating portion" here is not limited to a vent hole or the like that is formed in the passenger compartment, and is a concept that broadly encompasses portions that can be opened and closed, such as the windows and the sunroof and the like of the vehicle.

In a vehicle of a second aspect, in the vehicle of the first aspect, the discharging device is structured to include an air conditioner that takes in air of the passenger compartment interior or the passenger compartment exterior, and blows the air out into the passenger compartment interior.

In the vehicle of the second aspect, dust within the passenger compartment can be discharged to the passenger compartment exterior by using the air conditioner.

In a vehicle of a third aspect, in the vehicle of the second aspect, the control section discharges dust within the passenger compartment out to the passenger compartment exterior by a force that is stronger than at a time of operation of the air conditioner.

In the vehicle of the third aspect, the force of operation is changed between a force, at the time of discharging in a case in which the air conditioner is operated when adjusting the temperature of the passenger compartment interior, and a force at the time of discharging dust. Due thereto, at the time of discharging dust, the dust can reliably be discharged to the passenger compartment exterior.

In a vehicle of a fourth aspect, in the vehicle of any of the first through third aspects, at a time of operation of the discharging device or at a time before operation of the discharging device, the control section causes vibrating members that are provided in seats to vibrate.

In the vehicle of the fourth aspect, by causing the vibrating members to vibrate at the time of operation of the discharging device or at a time before operation of the discharging device, dust that sticks to the seats can be shaken off. Due thereto, even dust that sticks to the seats can be discharged to the passenger compartment exterior.

In a vehicle of a fifth aspect, in the vehicle of any of the first through fourth aspects, the control section includes a receiving section that receives a signal from the passenger compartment exterior, and the control section operates the discharging device in a case in which a signal to execute cleaning is received, by the receiving section, from the passenger compartment exterior.

In the vehicle of the fifth aspect, the discharging device is operated in a case in which a signal to execute cleaning is received from the passenger compartment exterior. Due thereto, in a state in which there are no occupants within the passenger compartment, cleaning of the passenger compartment interior can be made, from the exterior of the vehicle, to be carried out.

In a vehicle of a sixth aspect, in the vehicle of any of the first through fifth aspects, the control section forcibly stops the discharging device at a time of receiving a signal to release door locks, or at a time when a door is opened.

In the vehicle of the sixth aspect, the discharging device is forcibly stopped by the control section when a door is opened. Due thereto, the discharging device can be reliably stopped before a user enters into the vehicle.

In a vehicle of a seventh aspect, the vehicle of any of the first through sixth aspects further has at least one of a sanitizing device that sanitizes the passenger compartment interior, or an insecticidal device that kills pests within the passenger compartment interior.

In the vehicle of the seventh aspect, the environment of the passenger compartment interior can be maintained in a good state by at least one of a sanitizing device and an insecticidal device.

In a vehicle of an eighth aspect, in the vehicle of the seventh aspect, the sanitizing device is structured to include a sanitizing lamp that, by being lit, emits sanitizing light into the passenger compartment interior.

In the vehicle of the eighth aspect, by lighting the sanitizing lamp, the surfaces of the seats and the interior fitting members and the like within the passenger compartment can be sanitized.

A passenger compartment interior cleaning device of a ninth aspect is structured so as to be able to be mounted, from an exterior of a vehicle, to a communicating portion that is provided at the vehicle and communicates a passenger compartment interior with a passenger compartment exterior, and the passenger compartment interior cleaning device discharging at least one of dust or liquid which is within the passenger compartment through the communicating portion to the passenger compartment exterior in a state in which there are no occupants within the passenger compartment.

In the passenger compartment interior cleaning device of the ninth aspect, at least one of dust or liquid within the passenger compartment can be discharged through the communicating portion to the passenger compartment exterior. At this time, because the passenger compartment interior cleaning device is mounted to the communicating portion from the exterior of the vehicle, there is no need to provide a cleaning device at the vehicle. Further, because at least one of dust and liquid is discharged to the passenger compartment exterior in a case in which there are no vehicle occupants, cleaning can be carried out without causing the vehicle occupants discomfort.

As described above, the vehicle and the passenger compartment interior cleaning device relating to the present disclosure do not affect the vehicle occupants, while removing dust that is within the passenger compartment.

BRIEF DESCRIPTION OF THE DRAWINGS

Exemplary embodiments of the present disclosure will be described in detail based on the following figures, wherein.

DETAILED DESCRIPTION

First Embodiment

A vehicle 10 relating to a first embodiment is described with reference to the drawings. Note that the dimensional proportions in the drawings are exaggerated for convenience of explanation, and there are cases in which they differ from actual dimensional proportions.

Figure 1:
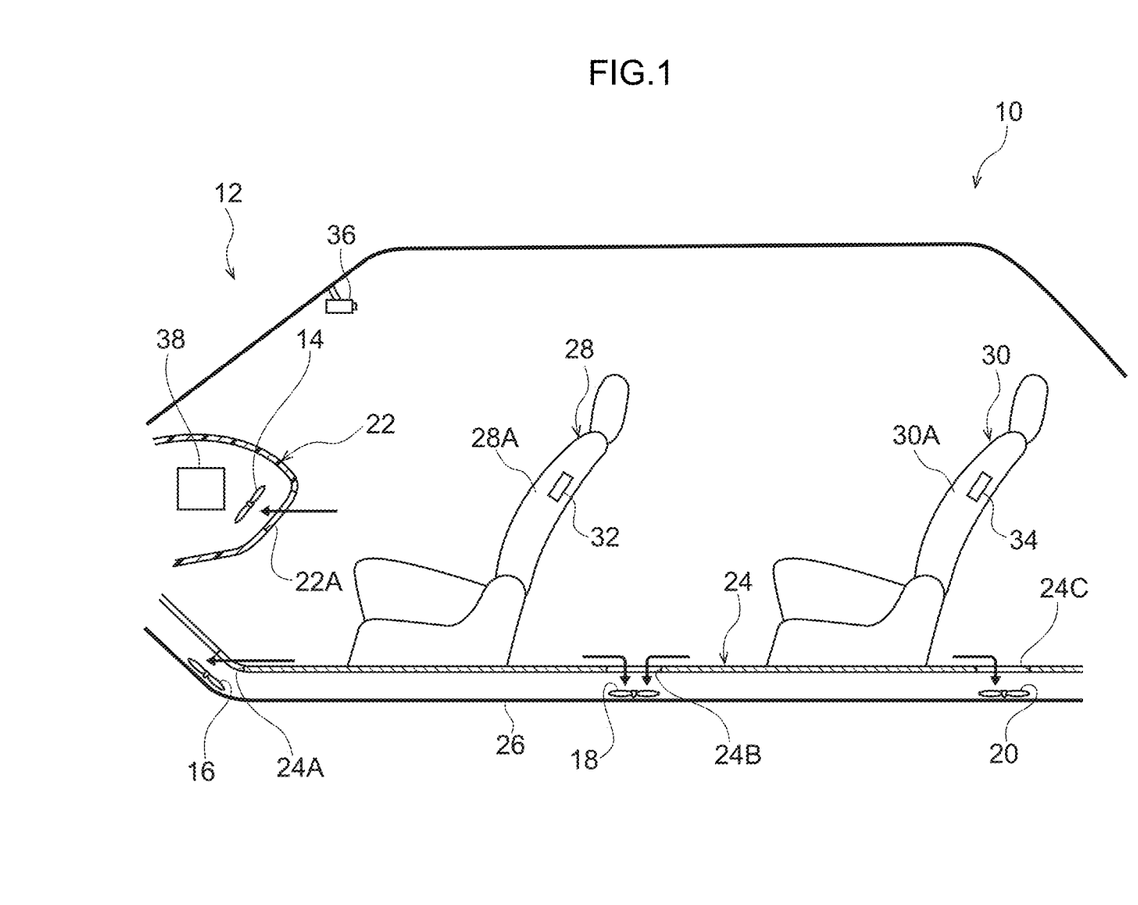
FIG. 1 is a side view showing main portions of a vehicle relating to a first embodiment.

As shown in FIG. 1, the vehicle 10 relating to the present embodiment has a passenger compartment interior cleaning unit 12. The passenger compartment interior cleaning unit 12 is structured to include four blowers that are a first blower 14, a second blower 16, a third blower 18 and a fourth blower 20 that serve as discharging devices, and front seat vibrators 32 and rear seat vibrators 34 that serve as vibrating members.

Note that, in the following explanation, when the four blowers that are the first blower 14, the second blower 16, the third blower 18 and the fourth blower 20 are referred to collectively without being differentiated, they are simply called "the blowers". Each of the blowers is structured so as to operate due to electric power being supplied thereto, and is electrically connected to an ECU (Electronic Control Unit) 38 that serves as a control section and is disposed at the vehicle front portion.

The first blower 14 is disposed at the inner side of an instrument panel 22 that is provided at the front portion of the passenger compartment interior. A first vent hole 22A that serves as a communicating portion is formed in the instrument panel 22. The passenger compartment interior and the passenger compartment exterior communicate via this first vent hole 22A. The first blower 14 faces the first vent hole 22A. Therefore, when the first blower 14 is operated, and the rotating blades of the first blower 14 are rotated in one direction, air within the passenger compartment is discharged through the first vent hole 22A to the passenger compartment exterior. In other words, air at the front side of the passenger compartment interior is drawn-in by the first blower 14.

Note that the first blower 14 of the present embodiment is structured such that the rotating blades thereof can rotate in the direction opposite to the one direction. Due to the rotating blades of the first blower 14 being rotated in the opposite direction, air can be blown-out into the passenger compartment. Here, an unillustrated air conditioner is provided at the inner side of the instrument panel 22. This air conditioner is structured so as to take-in air of the passenger compartment interior or the passenger compartment exterior, and adjust the temperature of the air, and blow the air out into the passenger compartment.

The second blower 16, the third blower 18 and the fourth blower 20 are disposed between a floor panel 24 and an under cover 26. The second blower 16 is positioned further toward the vehicle front side than front seats 28 as seen in plan view. A second vent hole 24A, a third vent hole 24B and a fourth vent hole 24C that serve as communicating portions are formed in the floor panel 24. The second blower 16 faces the second vent hole 24A that is formed in the front end portion of the floor panel 24. Therefore, when the second blower 16 is operated and the rotating blades of the second blower 16 are rotated in one direction, air within the passenger compartment is discharged out through the second vent hole 24A to the exterior of the passenger compartment. In other words, air at the front side of the passenger compartment interior is drawn-in by the second blower 16.

The third blower 18 is positioned between the front seats 28 and rear seats 30 as seen in plan view, and faces the third vent hole 24B that is formed in the vehicle longitudinal direction central portion of the floor panel 24. Therefore, when the third blower 18 is operated and the rotating blades of the third blower 18 are rotated in one direction, air within the passenger compartment is discharged out through the third vent hole 24B to the exterior of the passenger compartment. In other words, air at the longitudinal direction central portion of the passenger compartment interior is drawn-in by the third blower 18.

The fourth blower 20 is positioned further toward the vehicle rear side than the rear seats 30 as seen in plan view, and faces the fourth vent hole 24C that is formed in the vehicle longitudinal direction central portion of the floor panel 24. Therefore, when the fourth blower 20 is operated and the rotating blades of the fourth blower 20 are rotated in one direction, air within the passenger compartment is discharged out through the fourth vent hole 24C to the exterior of the passenger compartment. In other words, air at the rear side of the passenger compartment interior is drawn-in by the fourth blower 20.

As described above, the air, which is discharged out to the passenger compartment exterior by the first blower 14, the second blower 16, the third blower 18 and the fourth blower 20, flows toward the vehicle rear side in the space between the floor panel 24 and the under cover 26, and is discharged to the outer side from the rear portion of the vehicle 10.

Note that, in the present embodiment, the second blower 16, the third blower 18 and the fourth blower 20 are disposed in the space between the floor panel 24 and the under cover 26, but the present disclosure is not limited to this. For example, the second blower 16, the third blower 18 and the fourth blower 20 of the lower surface of the floor panel 24 may be mounted to regions at which the under cover 26 is not provided. In this case, the air at the passenger compartment interior is discharged directly to the outer side of the vehicle 10 by the second blower 16, the third blower 18 and the fourth blower 20.

Further, in the present embodiment, the second vent hole 24A, the third vent hole 24B and the fourth vent hole 24C may be structured so as to be able to be closed by unillustrated covers or the like. In this case, it may be made such that the second vent hole 24A, the third vent hole 24B and the fourth vent hole 24C are opened only when air at the passenger compartment interior is to be discharged.

The front seat vibrators 32 are installed within seatbacks 28A of the front seats 28. The front seat vibrators 32 are structured so as to, by being operated, vibrate, and cause the entire seatbacks 28A to vibrate, and can massage the vehicle occupants who are seated in the front seats 28. Further, by causing the front seat vibrators 32 to vibrate in a state in which vehicle occupants are not seated in the front seats 28, dust that sticks to the seatbacks 28A can be shaken off.

On the other hand, the rear seat vibrators 34 are installed within seatbacks 30A of the rear seats 30. The rear seat vibrators 34 are structured so as to, by being operated, vibrate, and cause the entire seatbacks 30A to vibrate, and can massage the vehicle occupants who are seated in the rear seats 30. Further, by causing the rear seat vibrators 34 to vibrate in a state in which vehicle occupants are not seated in the rear seats 30, dust that sticks to the seatbacks 30A can be shaken off. Note that the front seat vibrators 32 and the rear seat vibrators 34 are electrically connected to the ECU 38, and are operated by signals from the ECU 38.

Here, an onboard camera 36 is disposed at the front end of the ceiling portion within the passenger compartment. The onboard camera 36 faces toward the vehicle rear side and the vehicle lower side. The entire passenger compartment interior can be imaged by the onboard camera 36.

(Hardware Structures of Vehicle 10)

Figure 2:
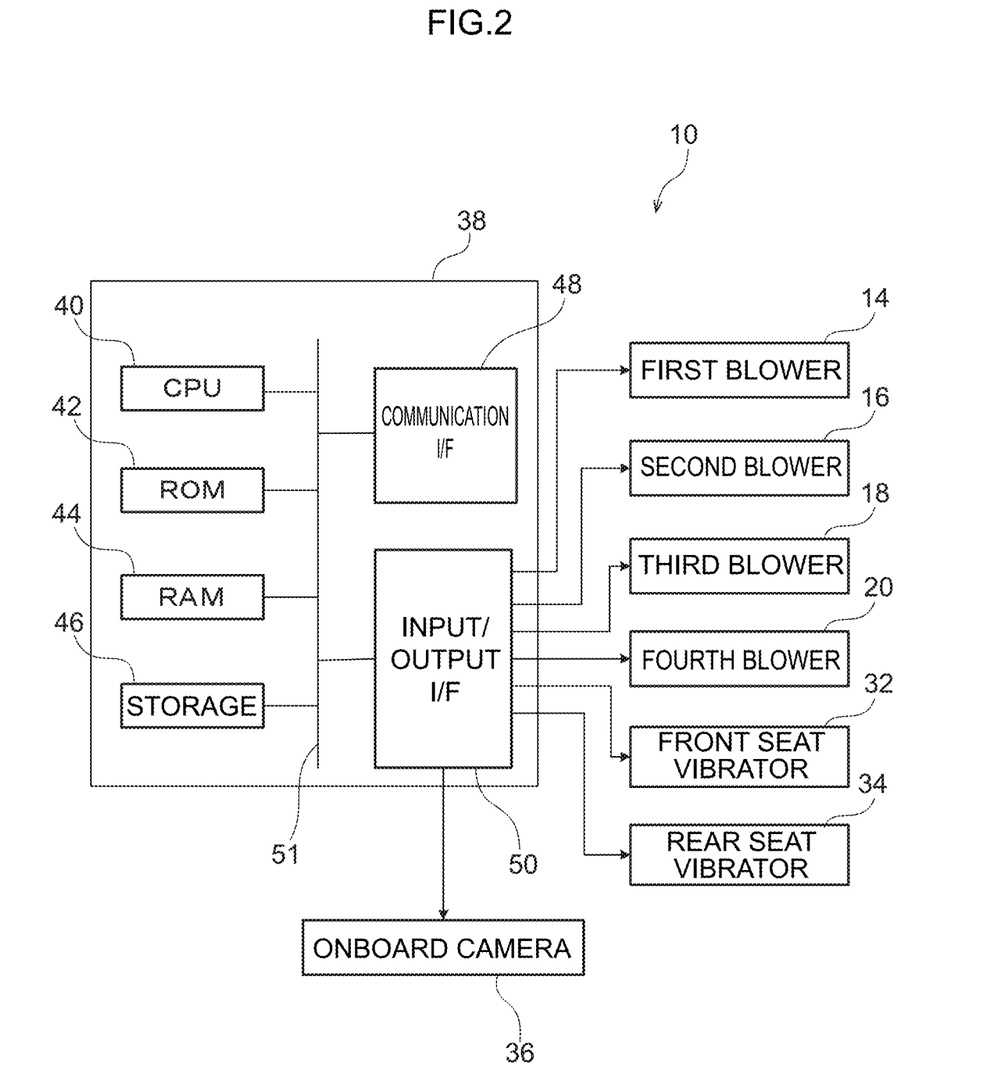
FIG. 2 is a block drawing showing hardware structures of the vehicle relating to the first embodiment.

FIG. 2 is a block drawing showing the hardware structures of the vehicle 10. As shown in FIG. 2, the vehicle 10 is structured to include a CPU (Central Processing Unit: a processor) 40, a ROM (Read Only Memory) 42, a RAM (Random Access Memory) 44, a storage 46, a communication interface 48 and an input/output interface 50. These respective structures are connected so as to be able to communicate with one another via a bus 51.

The CPU 40 is a central computing processing unit, and executes various programs and controls various sections. Namely, the CPU 40 reads-out programs from the ROM 42 or the storage 46, and executes the programs by using the RAM 44 as a workspace. The CPU 40 carries out control of the above-described respective structures and various computing processings in accordance with programs recorded in the ROM 42 or the storage 46.

The ROM 42 stores various programs and various data. The RAM 44 temporarily stores programs and data as a workspace. The storage 46 is structured by an HDD (Hard Disk Drive) or an SSD (Solid State Drive), and stores various programs including the operating system, and various data. In the present embodiment, a passenger compartment interior cleaning program, which is for cleaning the passenger compartment interior, and the like are stored in the ROM 42 or the storage 46.

The communication interface 48 is an interface for the vehicle 10 to communicate with external devices, and standards of Ethernet®, FDDI, Wi-Fi® or the like are used therefor.

The onboard camera 36, the first blower 14, the second blower 16, the third blower 18, the fourth blower 20, the front seat vibrators 32 and the rear seat vibrators 34 are connected to the input/output interface 50. Note that the onboard camera 36 is structured so as to receive a signal from the vehicle 10 and capture images of the passenger compartment interior. In the present embodiment, as an example, the onboard camera 36 images the passenger compartment interior while the power of the vehicle 10 is on.

(Functional Structures of Vehicle 10)

Various functions of the vehicle 10 are realized by using the above-described hardware structures. The functional structures realized by the vehicle 10 are described with reference to FIG. 3.

Figure 3:
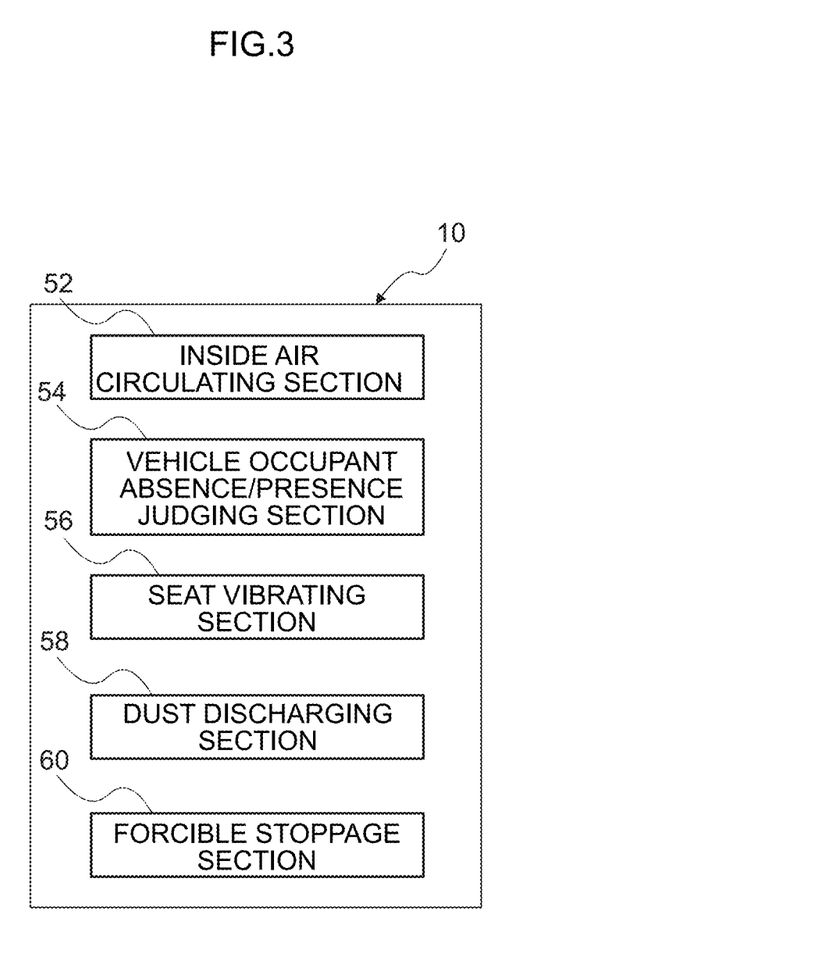
FIG. 3 is a block drawing showing functional structures of the vehicle relating to the first embodiment.

As shown in FIG. 3, the vehicle 10 is structured to include, as the functional structures thereof, an inside air circulating section 52, a vehicle occupant absence/presence judging section 54, a seat vibrating section 56, a dust discharging section 58 and a forcible stoppage section 60. Note that these respective functional structures are realized by the CPU 40 reading-out programs that are stored in the ROM 42 or the storage 46, and executing the programs.

The inside air circulating section 52 circulates the air that is within the passenger compartment. Concretely, by operating at least one blower among the first blower 14, the second blower 16, the third blower 18 and the fourth blower 20, the inside air circulating section 52 introduces air that is within the passenger compartment into the unillustrated air conditioner. Then, the inside air circulating section 52 circulates the air that is within the passenger compartment by again blowing-out, into the passenger compartment, the air whose temperature has been adjusted by the air conditioner.

The vehicle occupant absence/presence judging section 54 detects the absence/presence of vehicle occupants within the passenger compartment. Concretely, in a case in which the vehicle occupant absence/presence judging section 54 carries out analysis on the basis of the images captured by the onboard camera 36 and detects a vehicle occupant, the vehicle occupant absence/presence judging section 54 judges that there is a vehicle occupant within the passenger compartment. Further, in a case in which the vehicle occupant absence/presence judging section 54 carries out analysis on the basis of the images captured by the onboard camera 36 and does not detect a vehicle occupant, the vehicle occupant absence/presence judging section 54 judges that there are no vehicle occupants within the passenger compartment.

The seat vibrating section 56 vibrates the front seats 28 and the rear seats 30. Concretely, the seat vibrating section 56 causes the front seat vibrators 32 of the front seats 28 and the rear seat vibrators 34 of the rear seats 30 to vibrate at the time when the second blower 16, the third blower 18 and the fourth blower 20 are operated by the function of the dust discharging section 58 that is described later, or before the respective blowers operate. By vibrating the front seat vibrators 32 and the rear seat vibrators 34 in this way, the front seats 28 and the rear seats 30 are vibrated. Note that the present embodiment has a mode that massages the respective vehicle occupants who are seated in the front seats 28 and the rear seats 30. The seat vibrating section 56 vibrates the front seat vibrators 32 and the rear seat vibrators 34 at an output that is greater than in the case of the massaging mode.

The dust discharging section 58 operates the first blower 14, the second blower 16, the third blower 18 and the fourth blower 20, and draws-in air of the passenger compartment interior, and discharges dust that is within the passenger compartment to the exterior of the passenger compartment. At this time, the output at the time of operating the first blower 14, the second blower 16, the third blower 18 and the fourth blower 20 is made to be an output that is greater than that in the case in which the respective blowers are operated by the inside air circulating section 52. Namely, the dust within the passenger compartment can be discharged to the exterior of the passenger compartment due to the air within the passenger compartment being drawn-in by force that is stronger than in a case in which the respective blowers are operated by the inside air circulating section 52. In other words, the inside air circulating section 52 operates the respective blowers at an output that is lower than the output at which the blowers are operated by the dust discharging section 58. Further, the dust discharging section 58 operates the respective blowers in a case in which the vehicle occupant absence/presence judging section 54 judges that there are no vehicle occupants within the passenger compartment.

At the time of receiving a signal to unlock the door locks of the vehicle 10, or at the time when a door is opened, the forcible stoppage section 60 forcibly stops the respective blowers that are being operated by the dust discharging section 58. Concretely, in a case in which the first blower 14, the second blower 16, the third blower 18 and the fourth blower 20 are being operated by the function of the dust discharging section 58 in a state in which there are no vehicle occupants within the passenger compartment, the respective blowers are forcibly stopped at the time when a signal that unlocks the door locks is received from the exterior of the vehicle 10. Namely, the supply of electric power to the respective blowers is stopped even in a state that is in the midst of discharging dust.

(Operation)

Operation of the present embodiment is described next.

(Example of Passenger Compartment Interior Cleaning Processing)

Figure 4:
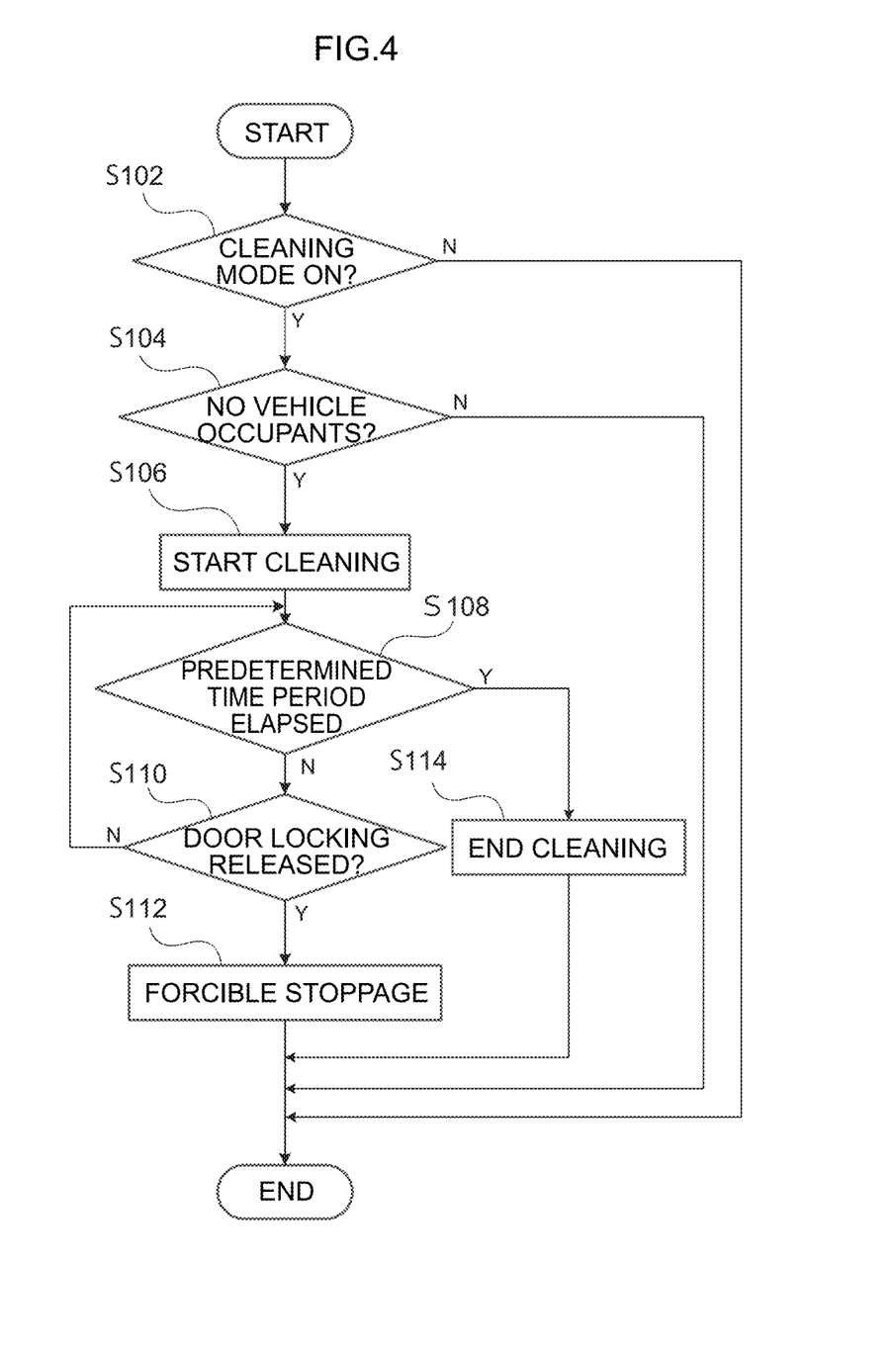
FIG. 4 is a flowchart showing an example of the flow of passenger compartment interior cleaning processing in the first embodiment.

FIG. 4 is a flowchart showing an example of the flow of passenger compartment interior cleaning processing by the vehicle 10. This passenger compartment interior cleaning processing is executed due to the CPU 40 reading-out the passenger compartment interior cleaning program from the ROM 42 or the storage 46, and expanding and executing the program in the RAM 44. Further, the passenger compartment interior cleaning processing is executed periodically at a predetermined time interval.

As shown in FIG. 4, in step S102 the CPU 40 judges whether or not the cleaning mode is on. For example, a button for switching the cleaning mode between on and off is provided at an unillustrated operation panel that is provided at the instrument panel 22, and the cleaning mode is switched by a vehicle occupant operating this button.

In a case in which the cleaning mode is set to on, in step S102, it is judged that the cleaning mode is on. On the other hand, in a case in which the cleaning mode is set to off, in step S102, it is judged that the cleaning mode is off. Note that there may be a structure in which the cleaning mode is switched by an operational method other than a button. For example, the cleaning mode may be displayed on a center display that is a touch panel, and the cleaning mode may be switched by a vehicle occupant touching the center display. Or, the cleaning mode may be switched by the voice of a vehicle occupant.

In a case in which the cleaning mode is on in step S102, the CPU 40 moves on to the processing of step S104. In a case in which the cleaning mode is not on in step S102, i.e., in a case in which the cleaning mode is off, the CPU 40 ends the passenger compartment interior cleaning processing without cleaning the interior of the passenger compartment.

In step S104, the CPU 40 judges whether or not there is a state in which there are no vehicle occupants in the passenger compartment. Concretely, the CPU 40 judges the absence/presence of vehicle occupants by using image data captured by the onboard camera 36 by the function of the vehicle occupant absence/presence judging section 54. If the CPU 40 judges that there are no vehicle occupants in the passenger compartment, the CPU 40 moves on to the processing of step S106. If the CPU 40 judges in step S104 that there is a vehicle occupant within the passenger compartment, the CPU 40 ends the passenger compartment interior cleaning processing without cleaning the interior of the passenger compartment.

In step S106, the CPU 40 starts cleaning of the passenger compartment interior. Concretely, the CPU 40 operates the first blower 14, the second blower 16, the third blower 18 and the fourth blower 20 by the function of the dust discharging section 58, and draws-in air that is within the passenger compartment. At this time, the respective blowers are operated at an output that is of an extent such that dust within the passenger compartment can be drawn-in.

Further, in step S106, by the function of the seat vibrating section 56, the CPU 40 causes the front seat vibrators 32, which are installed in the seatbacks 28A of the front seats 28, and the rear seat vibrators 34, which are installed in the seatbacks 30A of the rear seats 30, to vibrate. The time at which the front seat vibrators 32 and the rear seat vibrators 34 are vibrated is the time when the respective blowers are operated or before the respective blowers are operated.

Next, in step S108, the CPU 40 judges whether or not a predetermined time period has elapsed. This predetermined time period is a time period that is sufficient to carry out cleaning of the passenger compartment interior. The CPU 40 starts a timer from the start of cleaning in step S106, and clocks the time. When the CPU 40 judges that the predetermined time period has elapsed, the CPU 40 moves on to the processing of step S114.

In step S114, the CPU 40 ends cleaning. Namely, the CPU 40 stops the first blower 14, the second blower 16, the third blower 18 and the fourth blower 20. Further, the CPU 40 stops the front seat vibrators 32 and the rear seat vibrators 34. Then, the CPU 40 ends the passenger compartment interior cleaning processing.

On the other hand, in a case in which the CPU 40 judges in step S108 that the predetermined time period has not elapsed, the CPU 40 moves on to the processing of step S110, and judges whether or not locking of the doors of the vehicle 10 has been released. In a case in which a signal to unlock the door locks has been received from the exterior of the vehicle, the CPU 40 judges that locking of the doors of the vehicle 10 has been released, and moves on to the processing of step S112. In a case in which the CPU 40 judges in step S110 that the locking of the doors has not been released, the CPU 40 moves on to the processing of step S108, and repeatedly carries out judgment as to whether or not the predetermined time period has elapsed.

In step S112, the CPU 40 forcibly stops cleaning. Concretely, by the function of the forcible stoppage section 60, the CPU 40 stops the supply of electric power to the first blower 14, the second blower 16, the third blower 18 and the fourth blower 20. Further, the CPU 40 stops the supply of electric power to the front seat vibrators 32 and the rear seat vibrators 34. At this time, rotation of the respective blowers may be locked by locking mechanisms or the like. Namely, even in a case in which the supply of electric power to the respective blowers has been stopped, because the respective blowers are rotating due to inertia, rotation thereof may be locked forcibly. Then, the CPU 40 ends the passenger compartment interior cleaning processing.

In this way, in the vehicle 10 of the present embodiment, in a case in which it is judged by the vehicle occupant absence/presence judging section 54 that there are no vehicle occupants within the passenger compartment, the respective blowers are operated, air within the passenger compartment is drawn-in, and dust is discharged to the exterior of the passenger compartment. By discharging dust to the passenger compartment exterior in a case in which it is judged that there are no vehicle occupants within the passenger compartment in this way, dust that is within the passenger compartment can be discharged to the exterior thereof without causing discomfort to the vehicle occupants.

Further, in the present embodiment, because the respective blowers are operated and dust is discharged to the exterior of the passenger compartment, blowers that are used for other applications, such as for the air conditioner or the like, can be utilized, and there is no need to provide a dedicated cleaning device. For example, in FIG. 1, the first blower 14 can draw-in and circulate the air within the passenger compartment by making the output lower than in a case of sucking-in dirt. Due thereto, introduction of inside air and suction of dust can both be carried out by a single blower. Namely, dust within the passenger compartment can be removed at a low cost.

Moreover, in the present embodiment, by causing the front seat vibrators 32 and the rear seat vibrators 34 to vibrate at the time of operation of the respective blowers or before operation of the respective blowers, dust that has stuck to the front seats 28 and the rear seats 30 can be shaken off. Due thereto, dust within the passenger compartment can be removed effectively.

Still further, in the present embodiment, the respective blowers are forcibly stopped by the forcible stoppage section 60 at the time when a door is opened. Due thereto, the blowers can be stopped reliably before a user enters into the vehicle, and effects of the dust discharging section on vehicle occupants can be reduced.

Second Embodiment

A vehicle 70 relating to a second embodiment is described next with reference to FIG. 5 through FIG. 7. Note that structures that are similar to those of the first embodiment are denoted by the same reference numerals, and description thereof is omitted as appropriate.

Figure 5:
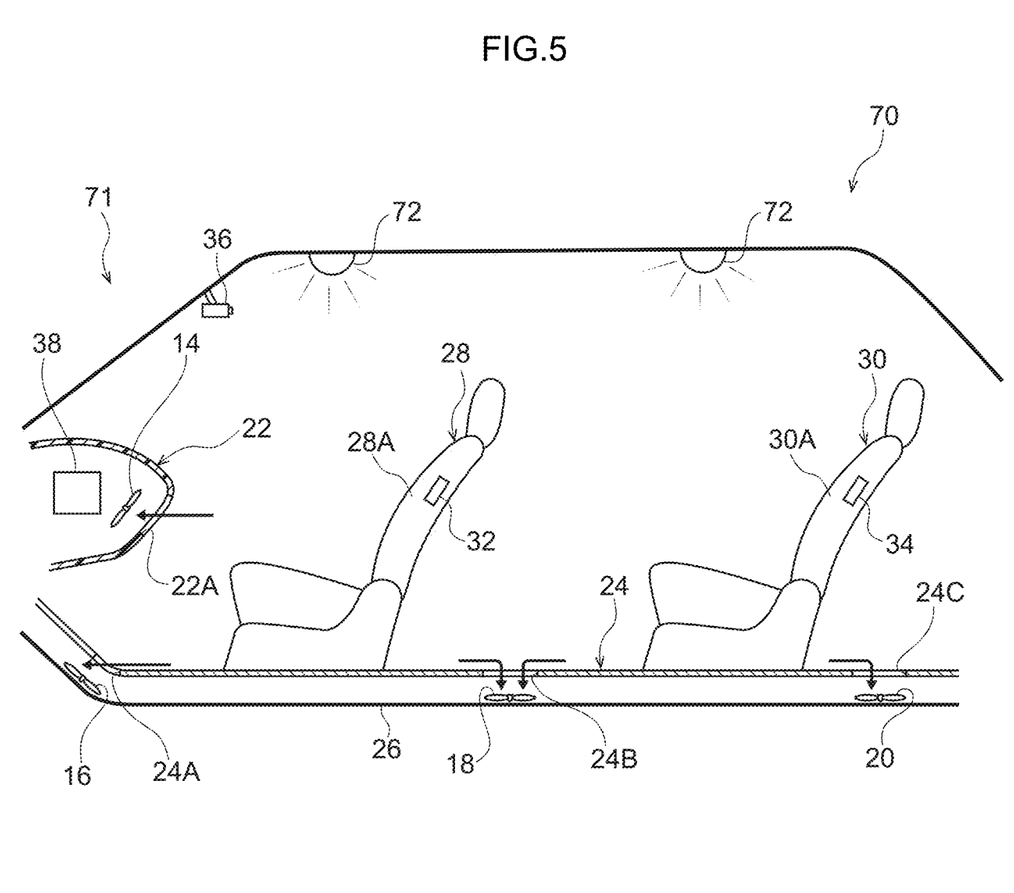
FIG. 5 is a side view showing main portions of a vehicle relating to a second embodiment.

As shown in FIG. 5, a passenger compartment interior cleaning unit 71 that is installed in the vehicle 70 relating to the present embodiment has sterilizing lamps 72, which serve as examples of a sterilizing device, in addition to the passenger compartment interior cleaning unit 12 of the first embodiment. In the present embodiment, as an example, the sterilizing lamps 72 are provided at the front portion and the rear portion, respectively, of the ceiling portion of the passenger compartment interior. The sterilizing lamps 72 are structured to include lamps that emit light rays (sterilizing light) of a predetermined wavelength that have sterilizing power. In the present embodiment, UV lamps (i.e., ultraviolet light emitting lamps) are used. Sterilizing light is emitted into the passenger compartment due to the sterilizing lamps 72 being lit.

(Hardware Structures of Vehicle 70)

Figure 6:
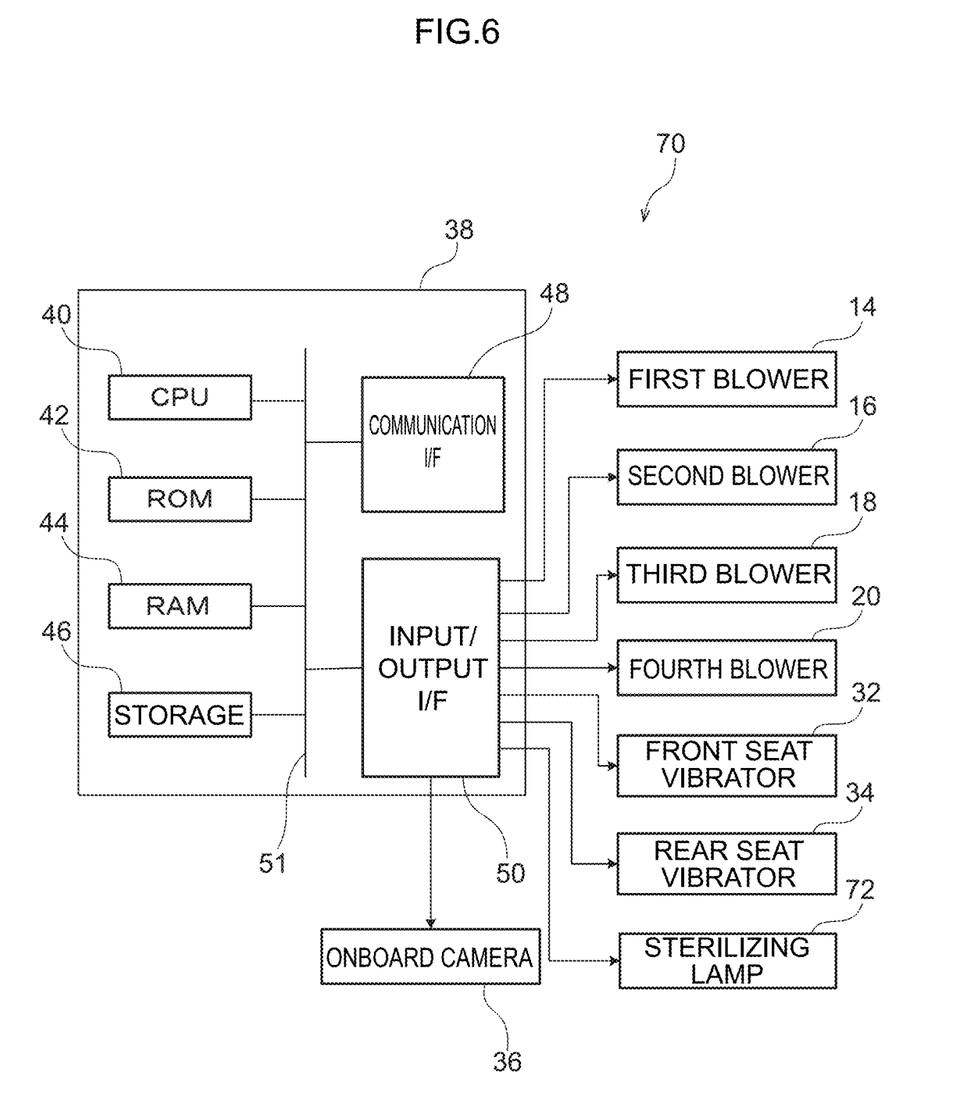
FIG. 6 is a block drawing showing hardware structures of the vehicle relating to the second embodiment.

FIG. 6 is a block drawing showing the hardware structures of the vehicle 70. As shown in FIG. 6, the vehicle 10 is structured to include the CPU 40, the ROM 42, the RAM 44, the storage 46, the communication interface 48 and the input/output interface 50. Further, the sterilizing lamps 72 (UV lamps) are connected to the input/output interface 50 of the present embodiment.

(Functional Structures of Vehicle 70)

Figure 7:
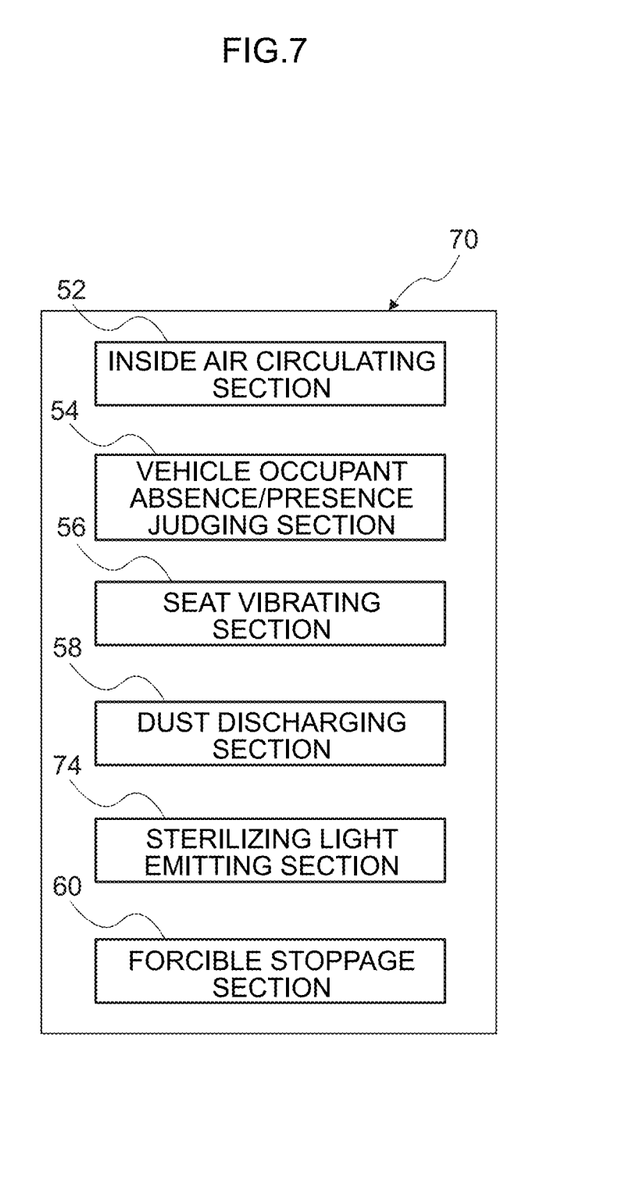
FIG. 7 is a block drawing showing functional structures of the vehicle relating to the second embodiment.

As shown in FIG. 7, the vehicle 70 is structured to include, as the functional structures thereof, the inside air circulating section 52, the vehicle occupant absence/presence judging section 54, the seat vibrating section 56, the dust discharging section 58, a sterilizing light emitting section 74, and the forcible stoppage section 60. Note that these respective functional structures are realized by the CPU 40 reading-out programs that are stored in the ROM 42 or the storage 46, and executing the programs.

In a case in which the vehicle occupant absence/presence judging section 54 judges that there are no vehicle occupants within the passenger compartment, the sterilizing light emitting section 74 lights the sterilizing lamps 72 that are within the passenger compartment, and thereby causes sterilizing light to be emitted within the passenger compartment. The other functional structures are similar to those of the first embodiment.

(Operation)

Operation of the present embodiment is described next.

(Example of Passenger Compartment Interior Cleaning Processing)

In the same way as in the first embodiment, the flow of the passenger compartment interior cleaning processing by the vehicle 70 is as per the flowchart shown in FIG. 4. This passenger compartment interior cleaning processing is executed due to the CPU 40 reading-out the passenger compartment interior cleaning program from the ROM 42 or the storage 46, and expanding and executing the program in the RAM 44. Further, the passenger compartment interior cleaning processing is executed periodically at a predetermined time interval.

Here, in the present embodiment, at the time when the CPU 40 starts cleaning in step S106, the CPU 40 operates the respective blowers, the front seat vibrators 32 and the rear seat vibrators 34 by the functions of the dust discharging section 58 and the seat vibrating section 56. Moreover, in the present embodiment, the front and rear sterilizing lamps 72 are lit and are made to emit sterilizing light into the passenger compartment by the function of the sterilizing light emitting section 74.

As described above, in the present embodiment, by lighting the sterilizing lamps 72, the front seats 28, the rear seats 30, the interior fitting members, and the like that are within the passenger compartment can be sterilized, and the environment within the passenger compartment can be maintained in an even better state.

Third Embodiment

A passenger compartment interior cleaning device 80 relating to a third embodiment is described next with reference to FIG. 8. Note that structures that are similar to those of the first embodiment are denoted by the same reference numerals, and description thereof is omitted as appropriate.

Figure 8:
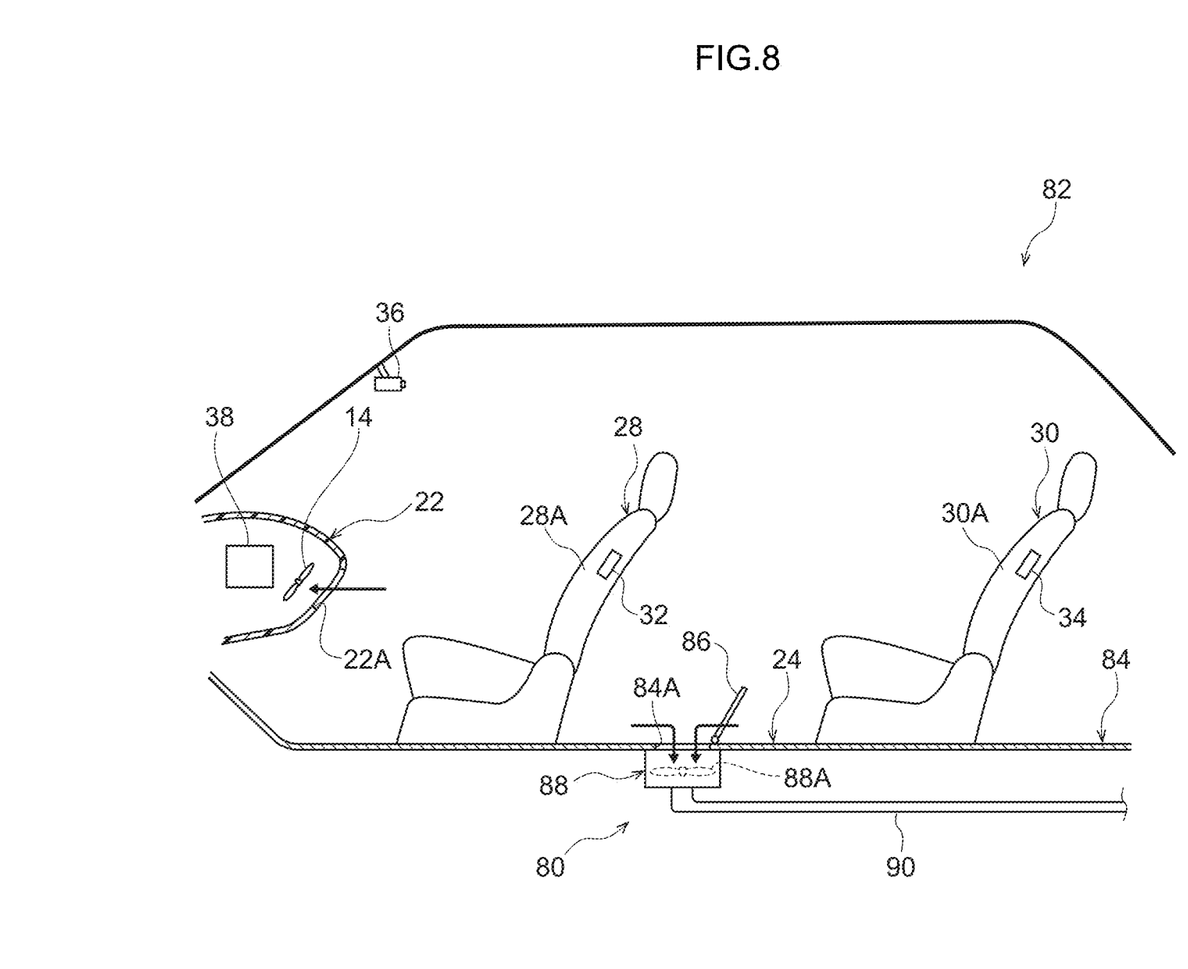
FIG. 8 is a schematic side view schematically showing a state in which a passenger compartment interior cleaning device relating to a third embodiment is mounted to a vehicle.

As shown in FIG. 8, the passenger compartment interior cleaning device 80 relating to the present embodiment is structured so as to be able to be mounted to a vehicle 82. Concretely, an exhaust hole 84A that serves as a communicating portion is formed in the vehicle longitudinal direction central portion of a floor panel 84 of the vehicle 82.

The exhaust hole 84A is formed so as to pass-through the floor panel 84, so as to communicate the interior of the passenger compartment and the exterior of the passenger compartment. The exhaust hole 84A can be opened and closed by a cover member 86. A state in which the cover member 86 is open and the exhaust hole 84A is open is shown in FIG. 8. Note that, as an example, the present embodiment is structured such that the cover member 86 and the floor panel 84 are flush with one another in the state in which the cover member 86 is closed.

Here, the passenger compartment interior cleaning device 80 is mounted from the exterior of the vehicle 82 to the bottom surface of the floor panel 84. The passenger compartment interior cleaning device 80 is structured to include an exhaust portion 88 and a duct portion 90. The exhaust portion 88 is formed substantially in the shape of a cylindrical tube. A vehicle exterior blower 88A is disposed at the interior of the exhaust portion 88. An unillustrated sealing member is provided at the top surface of the exhaust portion 88. Due to this sealing member being pushed against the bottom surface of the floor panel 84, the gap between the exhaust portion 88 and the floor panel 84 is sealed.

One end portion of the duct portion 90 is connected to the bottom surface of the exhaust portion 88, and the another end side extends from the exhaust portion 88 to the exterior of the vehicle. In the present embodiment, as an example, the another end side of the duct portion 90 extends from the exhaust portion 88 toward the vehicle rear side, and is connected to an unillustrated refuse collecting portion.

Here, as an example, the present embodiment is structured such that the first blower 14 is operated at the time when the vehicle exterior blower 88A is operated or before the vehicle exterior blower 88A is operated. Therefore, air is blown from the first vent hole 22A into the passenger compartment.

(Operation)

Operation of the present embodiment is described next.

In the passenger compartment interior cleaning device 80 of the present embodiment, due to the vehicle exterior blower 88A being operated in a state in which the passenger compartment interior cleaning device 80 is mounted to the vehicle 82, dust within the passenger compartment is discharged through the exhaust hole 84A to the exterior of the passenger compartment. Namely, dust flows through the duct portion 90 and is sent to the refuse collecting portion. In this way, because the passenger compartment interior cleaning device 80 is mounted from the exterior of the vehicle 82, there is no need to provide a separate cleaning device at the vehicle 82.

Further, in the present embodiment, air is drawn-in by the vehicle exterior blower 88A while air is blown-out into the passenger compartment interior from the first blower 14. Therefore, a flow of air can be generated within the passenger compartment, and dust can be discharged more effectively.

Although first through third embodiments have been described above, the present disclosure can, of course, be implemented in various forms within a scope that does not depart from the gist thereof. For example, the above-described embodiments are structured such that cleaning is carried out when there are no vehicle occupants within the passenger compartment, in the state in which the cleaning mode is set to on in advance. However, the present disclosure is not limited to this, and cleaning may be carried out by another method.

As an example of a method of carrying out cleaning of the passenger compartment interior, a structure may be employed in which a user transmits a signal to carry out cleaning to the vehicle 10, from the exterior of the vehicle. For example, there may be a structure in which the user of the vehicle 10 instructs cleaning of the passenger compartment interior due to the user operating a remote control key that he/she carries. In this case, a receiving section that receives signals from the exterior of the vehicle 10 may be provided. Further, the signal from the remote control key is received at the communication interface 48 of the ECU 38 by the function of this receiving section, and cleaning is started in a case in which it is judged, by the function of the vehicle occupant absence/presence judging section 54, that there are no vehicle occupants within the passenger compartment. Namely, the respective blowers are operated by the function of the dust discharging section 58. Further, the front seat vibrators 32 and the rear seat vibrators 34 may be vibrated by the function of the seat vibrating section 56. At this time, in a case in which the doors of the vehicle 10 are not locked, locking of the doors may be carried out before cleaning is started.

Further, in the above-described embodiments, air within the passenger compartment is drawn-in due to the four blowers, which are the first blower 14, the second blower 16, the third blower 18 and the fourth blower 20, being operated. However, the number of blowers is not particularly limited. For example, there may be a structure that is provided within only the first blower 14, and air within the passenger compartment may be drawn-in by this one blower only. Conversely, there may be a structure having five or more blowers. Further, the positions of the respective blowers also are not limited. For example, a blower may be provided at the ceiling portion, and air may be drawn-in toward the vehicle upper side.

Moreover, in the above-described embodiments, the first vent hole 22A, the second vent hole 24A, the third vent hole 24B and the fourth vent hole 24C are the communicating portions. However, the present disclosure is not limited to this, and, for example, a window or the sunroof or the like of the vehicle 10 may be used as a communicating portion. In this case, dust within the passenger compartment can be discharged by mounting a discharging device from the exterior of the vehicle 10 and operating the discharging device, in the state in which the window or the sunroof or the like is open. Further, by making the passenger compartment interior be positive pressure, dust within the passenger compartment may, together with air within the passenger compartment, be discharged to the passenger compartment exterior.

Moreover, although the above embodiments describe structures in which air within the passenger compartment is drawn-in, the present disclosure is not limited to this. Namely, a discharging device, which discharges at least one of dust and liquid to the exterior of the passenger compartment, may be used. For example, a discharging device such as a suction pump or the like may be used instead of the blower. In this case, by operating the suction pump after the passenger compartment interior is washed with water, liquid within the passenger compartment can be discharged (drained) to the passenger compartment exterior. Further, a nozzle that sprinkles water, such as a sprinkler or the like, may be provided at the ceiling portion of the passenger compartment interior, and, after water is sprinkled from this nozzle into the passenger compartment, the suction pump may be operated and the water drained.

Still further, the above-described first embodiment and second embodiment are structures in which dust within the passenger compartment is removed by utilizing the blowers that are operated at the time of circulating air that is within the passenger compartment by the inside air circulating section 52. However, the present disclosure is not limited to this. For example, there may be a structure in which dust within the passenger compartment is removed by using another blower that is installed in the vehicle 10. In this case, in the same way as in the above-described embodiments, dust within the passenger compartment is removed by operating the blower at an output, which is higher than the output that is usually used, in a state in which there are no vehicle occupants within the passenger compartment.

Further, in the above embodiments, the front seat vibrators 32 are installed in the seatbacks 28A of the front seats 28, and the rear seat vibrators 34 are installed in the seatbacks 30A of the rear seats 30, but the present disclosure is not limited to this. For example, vibrators that are similar to the front seat vibrators 32 may be installed also in the seat cushions and the headrests of the front seats 28.

Moreover, in addition to the above-described structures, a cleaning device that cleans the floor panel 24 may be provided. For example, a cleaning device that takes-in dust while traveling automatically on the floor panel 24 may be provided. In this case, after the first blower 14, the second blower 16, the third blower 18 and the fourth blower 20 are operated by the function of the dust discharging section 58, and the dust within the passenger compartment is moved downward, the dust on the floor panel 24 is taken-in by the cleaning device, and the dust can thereby be removed efficiently.

Still further, in the above-described embodiments, the occupant absence/presence judging section judges the absence/presence of vehicle occupants from images captured by the onboard camera 36. However, the present disclosure is not limited to this. For example, seating sensors may be provided at the respective seats, and, in a case in which it is sensed that there are no vehicle occupants seated in any of the seats from the signals of these seating sensors, it may be judged that there are no vehicle occupants within the passenger compartment. Further, other sensor types may be provided at the respective seats, and the absence/presence of vehicle occupants may be judged by these sensors.

The above-described third embodiment is structured such that the exhaust hole 84A is formed in the floor panel 84, and the passenger compartment interior cleaning device 80 is mounted to the portion where this exhaust hole 84A is formed. However, the present disclosure is not limited to this, and may be structured such that, for example, a vent hole is formed in the ceiling portion of the vehicle 82, and a passenger compartment interior cleaning device is mounted to the ceiling portion from the upper side of the vehicle 82. In this case, an unmanned flying object such as a drone or the like that is equipped with a venting function may be used.

Moreover, the above-described second embodiment is structured such that the front seats 28, the rear seats 30, the interior fitting members, and the like of the passenger compartment interior are sterilized due to the sterilizing lamps 72 being lit. However, the present disclosure is not limited to this, and another sterilizing device may be used. For example, the sterilizing device may be structured to include a sterilizing sprayer or the like that sprinkles a germicide. Further, there may be a structure in which an insecticidal device that kills pests within the passenger compartment is provided instead of a sterilizing device, or in addition to a sterilizing device.

Note that any of various types of processors other than a CPU may execute the passenger compartment interior cleaning processing that the CPU 40 executes by reading-in and executing software (programs) in the above-described embodiments. Examples of processors in this case include PLDs (Programmable Logic Devices) whose circuit structure can be changed after production such as FPGAs (Field-Programmable Gate Arrays) and the like, or dedicated electrical circuits that are processors having circuit structures that are designed for the sole purpose of executing specific processings such as ASICs (Application Specific Integrated Circuits) and the like, or the like. Further, the passenger compartment interior cleaning processing may be executed by one of these various types of processors, or may be executed by combining two or more of the same type or different types of processors (e.g., plural FPGAs, or a combination of a CPU and an FPGA, or the like). Further, the hardware structures of these various types of processors are, more concretely, electrical circuits that combine circuit elements such as semiconductor elements and the like.

Still further, in the above-described embodiments, the storage 46 is the recording section, but the present disclosure is not limited to this. For example, a recording medium such as a CD (Compact Disk), a DVD (Digital Versatile Disk), a USB (Universal Serial Bus) memory, or the like may be used as the recording section. In this case, the various programs are stored on the recording medium.

What is claimed is:

1. A vehicle, comprising:
    a communicating portion that communicates a passenger compartment interior with a passenger compartment exterior;
    a discharging device that, by operating, discharges at least one of dust or liquid which is within the passenger compartment interior through the communicating portion to the passenger compartment exterior; and a control section that, in a case of determining that there are no vehicle occupants within the passenger compartment interior, operates the discharging device, and causes dust within the passenger compartment interior to be discharged to the passenger compartment exterior; wherein the discharging device is structured to include an air conditioner that takes in air of the passenger compartment interior or the passenger compartment exterior, and blows the air out into the passenger compartment interior, and the control section discharges dust within the passenger compartment interior out to the passenger compartment exterior by a force that is stronger than at a time of operation of the air conditioner.

2. The vehicle of claim 1, wherein, at a time of operation of the discharging device or at a time before operation of the discharging device, the control section causes vibrating members that are provided in seats to vibrate.

3. The vehicle of claim 1, wherein:
the control section includes a receiving section that receives a signal from the passenger compartment exterior; and
the control section operates the discharging device in a case in which a signal to execute cleaning is received, by the receiving section, from the passenger compartment exterior.

4. The vehicle of claim 1, wherein the control section forcibly stops the discharging device at a time of receiving a signal to release door locks, or at a time when a door is opened.

5. The vehicle of claim 1, further comprising at least one of a sanitizing device that sanitizes the passenger compartment interior, or an insecticidal device that kills pests within the passenger compartment interior.

6. The vehicle of claim 5, wherein the sanitizing device is structured to include a sanitizing lamp that, by being lit, emits sanitizing light into the passenger compartment interior.

7. A vehicle, comprising:
a communicating portion that communicates a passenger compartment interior with a passenger compartment exterior;
a discharging device that, by operating, discharges at least one of dust or liquid which is within the passenger compartment interior through the communicating portion to the passenger compartment exterior; and
a control section that, in a case of determining that there are no vehicle occupants within the passenger compartment interior, operates the discharging device, and causes dust within the passenger compartment interior to be discharged to the passenger compartment exterior, wherein
at a time of operation of the discharging device or at a time before operation of the discharging device, the control section causes vibrating members that are provided in seats to vibrate.

* * * * *